United States Patent [19]

Bretschneider et al.

[11] 4,005,100

[45] Jan. 25, 1977

[54] PYRAZOLE-5-CARBOXAMIDES

[75] Inventors: Hermann Bretschneider; Wilhelm Klotzer, both of Innsbruck, Austria; Gunther Bader, Grafelfing-Lochham, Germany; August Lutz, Birsfelden, Switzerland

[73] Assignee: Hoffmann-La Roche Inc., Nutley, N.J.

[22] Filed: Jan. 15, 1975

[21] Appl. No.: 541,184

Related U.S. Application Data

[62] Division of Ser. No. 335,396, Feb. 23, 1973, Pat. No. 3,875,182.

[30] Foreign Application Priority Data

Feb. 28, 1972 Switzerland .................... 2769/72

[52] U.S. Cl. .................................. 260/310 R
[51] Int. Cl.$^2$ ................................ C07D 403/12
[58] Field of Search ......................... 260/310 R

[56] References Cited

UNITED STATES PATENTS 3,564,010   2/1971   Bretschneider et al. ..... 260/346.47

OTHER PUBLICATIONS

Musante, Gazz. Chim. Ital. vol. 78, pp. 178–181 & 186 (1948).
Wiley (ed.) "Pyrazoles, Pyrazolines, Pyrazolidines, Indazoles and Condensed Rings," (1967). Interscience Publishers, (p. 116).

Primary Examiner—Donald B. Moyer
Attorney, Agent, or Firm—Samuel L. Welt; Bernard S. Leon; William H. Epstein

[57] ABSTRACT

3-Methyl-N-(1-pyrrolin-2-yl)-pyrazole-5-carboxamides and processes for making same. Such compounds lower blood sugar and, hence, are useful as antidiabetic agents.

3 Claims, No Drawings

PYRAZOLE-5-CARBOXAMIDES

This is a division of application Ser. No. 335,396 filed Feb. 23, 1973, now U.S. Pat. No. 3,875,182.

DETAILED DESCRIPTION OF THE INVENTION

The present invention relates to a novel pyrazole carboxamide derivatives of the formula

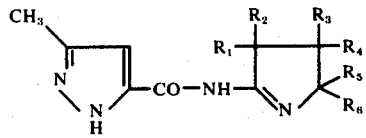

wherein $R_1$ and $R_2$ represent phenyl, lower alkyl phenyl or lower alkoxy phenyl and $R_3$, $R_4$, $R_5$ and $R_6$ are each selected from the group consisting of hydrogen and lower alkyl and to processes for the preparation of such compounds.

The term "lower alkyl" as utilized herein represent both a straight or branched chain lower alkyl grouping containing 1 to 7, most preferably, 1 to 3 carbon atoms, such as methyl, ethyl, propyl and the like. An especially preferred alkyl group for the purposes of the present invention is methyl. Also, preferred are compounds of the formula I wherein $R_1$ and $R_2$ are phenyl. Thus, in a particularly preferred embodiment, compounds of the formula I are selected from the group in which $R_1$ and $R_2$ are phenyl and $R_3$, $R_4$, $R_5$ and $R_6$ each represent hydrogen or methyl.

An especially preferred compound is the compound wherein $R_1$ and $R_2$ each are phenyl; $R_3$, $R_4$ and $R_5$ are hydrogen and $R_6$ is methyl, i.e. a compound of the formula 3-methyl-N-(5-methyl-3,3-diphenyl-1-pyrrolin-2-yl)-pyrazole-5-carboxamide.

The compound of the formula I is prepared via the reaction of a compound of the formula

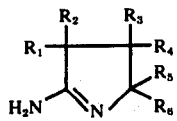

wherein $R_1$, $R_2$, $R_3$, $R_4$, $R_5$ and $R_6$ have the same significance as ascribed thereto hereinabove with a reactive derivative of 3-methylpyrazole-5-carboxylic acid. By the expression "reactive derivative" as utilized herein, there is intended a functional derivative of 3-methyl-pyrazole-5-carboxylic acid such as an ester (phenyl esters and alkyl esters, preferably, lower alkyl esters), a dimer, an anhydride or any derivative of 3-methyl-pyrazole-5-carboxylic acid which is more reactive to a compound of the formula II than the free acid.

Among the many reactive derivatives of 3-methyl-pyrazole-5-carboxylic acid which are suitable for the purposes of the present invention, there can be included 2,7-dimethyl-4,9-dioxo-4H,9H-dipyrazolo[1,5-a:1',5'-d]pyrazine of the formula

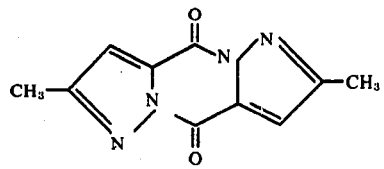

obtained by reacting 3-methyl-pyrazole-5-carboxylic acid with thionyl chloride as described in Ber. 61 (1928) 2408.

The reaction of a compound of the formula II with a reactive derivative of 3-methylpyrazole-5-carboxylic acid is effected by warming a compound of the formula II in the presence of an inert organic solvent. Of the many suitable solvents, preferred is dimethylformamide. Other solvents which are suitable for the purposes of the present invention include hydrocarbons, such as benzene; aliphatic hydrocarbons such as petroleum ether; chlorinated hydrocarbons such as chloroform; ethers such as dioxane or tetrahydrofuran; lower alkanols such as ethanol and the like.

Compounds of the formula II can also exist in the tautomeric form

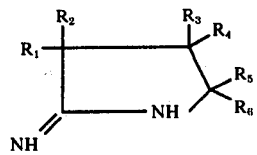

wherein $R_1$, $R_2$, $R_3$, $R_4$, $R_5$ and $R_6$ are as above and this form is as efficacious for the purposes of the present invention as is the form illustrated in formula II above.

Compounds of the formula I above lower the blood sugar level of warm-blooded animals upon oral administration and, hence, are useful as antidiabetics.

A compound encompassed by the formula I, namely, 3-methyl-N-(5-methyl-3,3-diphenyl-pyrrolin-2-yl)pyrazole-5-carboxamide, upon oral administration to maximal streptozotocin-diabetic rats gave the following values for the glucose and fatty acid levels (in % of controls):

Table

| Dosage | Glucose | | | Free fatty acids | | | Hours after application |
|---|---|---|---|---|---|---|---|
| [μmol/kg] | 2 | 4 | 6 | 2 | 4 | 6 | |
| 100 | 70 | 80 | 60[*] | — | — | — | [*] |
|  | — | 96 | — | — | 56 | — | |
|  | — | 50 | — | — | — | — | |
| 300 | 76 | 77 | 71 | 59 | 72 | 50 | |
|  | 70 | 79 | 59 | — | — | — | |
|  | — | 78 | — | — | 62 | — | |
|  | — | 51 | — | — | — | — | |
|  | — | 30 | — | — | — | — | |
| 1000 | — | 89 | — | — | 57 | — | |
|  | — | 80 | — | — | — | — | |

[*]Values for the glucose and fatty acid levels in % of controls

The test procedure was that described by E. LORCH in Diabetologia 7, 195–203 (1971).

Female (140–160 gr) Albino-rats were starved (24 hrs) and refed (16 hrs) one week after Streptozotocin administration (60 mg/kg s.c.). Mean plasma glucose values: 500–600 mg/100 ml plasma. Diabetic starved-refed control animals received the suspension vehicle alone.

The DL$_{50}$ in the rat amounts to 8 g/kg (single oral application: observation period 10 days).

The compounds of the formula I can be used in conventional pharmaceutical dosage forms with the dosage adjusted to suit the exergencies of a particular situation. They can be compounded into conventional pharmaceutical preparations which contain a compound of the formula I in admixture with a pharmaceutically compatible carrier. Such carrier can be an organic or inorganic inert carrier material suitable for enteral or parenteral application such as water, gelatin, gum arabic, lactose, starch, magnesium stearate, talc and the like. The pharmaceutical preparations can be present in the form of tablets, dragees, suppositories, capsules and the like.

The following examples are illustrative of the invention. All temperatures are stated in degrees Centigrade.

EXAMPLE 1

1.08 g of 2,7-dimethyl-4,9-dioxo-4H,9H-dipyrazolo[1,5-a: 1',5'-d]pyrazine are suspended in 35 ml of absolute dimethyl-formamide, treated with 2.36 g of 3,3-diphenyl-2-amino-pyrroline-(1) and the resultant medium is warmed on a boiling water bath for 5 hours. After 30 minutes, complete solution sets in. The solvent is then removed as completely as possible in a vacuum. The oil which remains is dissolved in 80 ml of chloroform. This solution is extracted successively with two 30 ml portions of 5% acetic acid and two 30 ml portions of 5% sodium bicarbonate solution in order to remove unreacted starting materials. The chloroform phase is washed with water and dried and the chloroform is then removed in a vacuum. The residual oil crystallizes upon trituration with a small amount of petroleum ether yielding 3-methyl-N-(3,3-diphenyl-1-pyrrolin-2-yl)-pyrazole-5-carboxamide of melting point 213°–215° C. (from ethanol).

EXAMPLE 2

2.16 g of 2,7-dimethyl-4,9-dioxo-4H,9H-dipyrazolo[1,5-a: 1',5'-d]pyrazine are suspended in 80 ml of absolute dimethylformamide. The resultant medium is treated with 5 g of 2-amino-3,3-diphenyl-5-methyl-pyrroline-(1) and then warmed on a boiling water-bath for 5 hours. After 1 hour, complete solution sets in. The solvent is then completely distilled off in a vacuum and the yellow-brown oil is dissolved in 100 ml of chloroform. This solution is extracted successively with three 30 ml portions of 5% acetic acid and three 30 ml portions of 5% sodium bicarbonate solution in order to remove unreacted starting materials. The chloroform phase is washed with water and dried and the chloroform is then removed in a vacuum. The residual oil can be crystallized by trituration with a small amount of ethanol to give 3-methyl-N-(5-methyl-3,3-diphenyl-1-pyrrolin-2-yl)-pyrazole-5-carboxamide of melting point 221°–223° C. (from ethanol).

EXAMPLE 3

528 mg of 2-amino-3,3-diphenyl-5,5-dimethyl-pyrroline-(1) in 8 ml of absolute dimethylformamide are heated for 3 hours on a boiling water bath under anhydrous conditions with 230 mg of 2,7-dimethyl-4,9-dioxo-4H,9H-dipyrazolo[1,5-a: 1',5'-d]pyrazine. The dimethylformamide is removed by distillation in a vacuum on a water bath. The residue remaining after distillation is taken up in 15 ml of chloroform and the solution is washed twice with 5% acetic acid, once with water, once with dilute sodium bicarbonate solution and again with water. The residue obtained after drying and evaporation of the solvent is digested with a small amount of cold ether, filtered and recrystallized from acetonitrile and alcohol yielding 3-methyl-N-(5,5-dimethyl-3,3-diphenyl-1-pyrrolin-2-yl)-pyrazole-5-carboxamide of melting point 193°–195° C.

EXAMPLE 4

1.08 g of 2,7-dimethyl-4,9-dioxo-4H,9H-dipyrazolo[1,5-a: 1',5'-d]pyrazine are suspended in 40 ml of absolute dimethyl-formamide treated with 2.64 g of 3,3-di(p-tolyl)-2amino-pyrroline-(1) and warmed on a boiling water bath for 5 hours. After complete solution has set in, all of the solvent is removed in a vacuum. The crystallized residue which remains is dissolved in 100 ml of warm chloroform. After cooling the solution to room temperature, it is extracted successively with two 30 ml portions of 5% acetic acid and two 30 ml portions of 5% sodium bicarbonate solution in order to remove unreacted starting materials. The chloroform phase is washed with water, dried and evaporated. The crystalline residue is boiled up with 40 ml of ethanol and filtered, yielding 3-methyl-N-[3,3-di(p-tolyl)-1-pyrrolin-2-yl]-pyrazole-5-carboxamide of melting point 243°–245° C. The product recrystallizes from ethylene glycol monomethyl ether.

EXAMPLE 5

15.5 g of 2-amino-3,3-bis(p-methoxyphenyl)-5-methyl-1-pyrroline and 5.4 g of 2,7-dimethyl-4H,9H-dipyrazolo[1,5-a: 1',5'-d]pyrazine are suspended in 100 ml of absolute dimethyl-formamide and warmed to 120° C. for 5 hours with intensive stirring and exclusion of moisture, a clear solution being obtained. The dimethylformamide is subsequently distilled off in a water-jet pump vacuum and the remaining residue is dissolved in 250 ml of chloroform. This chloroform solution is washed twice with 5% acetic acid, twice with ca 10% sodium bicarbonate solution and subsequently with water. After evaporation of the chloroform, a crude product remain behind. Upon recrystallization of the crude product from benzene/low boiling petroleum ether, there is obtained N-[3,3-bis(p-methoxyphenyl)-5-methyl-1-pyrrolin-2-yl]-5-methylpyrazole-3-carboxamide of melting point 173° C. (uncorrected).

The starting material can be prepared as follows:

253 g of bis(p-methoxyphenyl)acetonitrile are introduced into a suspension of 40.6 g of sodium amide in 3000 ml of absolute benzene and intensively stirred for 0.5 hour at 70° C. while passing a dry nitrogen stream through the reaction medium. Ammonia is thereby driven out. By applying a partial vacuum, any ammonia residues are removed. 122 g of methacrylic acid methyl ester are then introduced and condensed for 5 hours under a nitrogen atmosphere and with intensive stirring. After cooling, the resultant mixture is carefully treated with water, washed out, washed with 5% acetic acid and subsequently with 10% sodium bicarbonate solution. After evaporation of the benzene in a water-jet vacuum, there is obtained 4,4-[bis(p-methoxyphenyl)]-4-cyano-2-methyl-butyric acid methyl ester as a viscous oil. The crude ester can be saponified directly to the acid.

330 g of the thus-prepared 4,4-[bis(p-methoxyphenyl)]-4-cyano-2-methyl-butyric acid methyl ester are suspended in a solution of 220 g of sodium hydroxide in 2000 ml of water and warmed to 90° C. for 2 hours. An almost clear solution results. After clear filtration of the cooled solution, the filtrate is made just Congo-acid with 15% hydrochloric acid with the addition of ice and 4,4-[bis(p-methoxyphenyl)]-4-cyano-2-methyl-butyric acid separates out in crystalline form. The product after recrystallization from benzene/petroleum ether has a melting point 138° C.

339 g (0.1 mol) of the thus-obtained 4,4-[bis(p-methoxyphenyl)]-4-cyano-2-methyl-butyric acid are treated with the same part by weight of thionyl chloride and the mixture is warmed to 70° C. for 0.5 hour with stirring. Gaseous hydrogen chloride and sulfur dioxide thereby evolve. The resultant medium is then evacuated and evaporated twice in a vacuum with a small amount of benzene in order to remove the residues of thionyl chloride by azeotropic distillation. The resulting crude acid chloride solidifies upon storage in a refrigerator to crystals which melt at ca 40° C. The thus-obtained crude acid chloride, namely, 4,4-[bis(p-methoxyphenyl)]-4-cyano-2-methyl butyric acid chloride can be used in the following step without further purification.

The thus-prepared 4,4-[bis(p-methoxyphenyl)]-4-cyano-2-methyl butyric acid chloride is dissolved in 75 ml of dry acetone and treated dropwise at 0° C. with a freshly prepared cold solution of 6.5 g of sodium azide in 22 ml of water and subsequently stirred at 0° C. for 1 hour. The mixture is then introduced into ca 200 ml of ice/water. The 4,4-[bis(p-methoxyphenyl)]-4-cyano-2-methyl-butyric acid azide separates out in the form of oil droplets. These are taken up in 120 ml of benzene, washed with cold water and dried over sodium sulfate. The thus-obtained solution contains the azide which is decomposed by warming and by boiling to reflux for 0.5 hour. Evolution of nitrogen occurs during this decomposition. After evaporation of the benzene, there remains behind 3,3-[bis(p-methoxyphenyl)]-3-cyano-1-methyl-propylisocyanate in the form of a viscous oil.

The thus-obtained crude 3,3-[bis(p-methoxyphenyl)]-3-cyano-1-methyl-propyl-isocyanate is added to a solution of one part by weight of potassium hydroxide in four parts by volume of methanol and boiled at reflux for 1 hour with stirring. The main amount of methanol is subsequently removed under reduced pressure and treated with 500 ml of ice-water, made just Congo-acid at ca 5° to 10° C. with 15% hydrochloric acid, washed clear with a small amount of ether and the clear aqueous phase is made alkaline with 10% sodium hydroxide. The 2-amino-3,3-[bis(p-methoxyphenyl)]-5-methyl-1-pyrroline which initially separates out in the form of an oil soon solidifies to clumps. The clumps are extracted twice with 200 ml of methylene chloride and dried over sodium sulfate. The solid residue remaining behind after evaporation of the solvent is recrystallized from benzene/petroleum ether giving 4,4-[bis(p-methoxyphenyl)]-4-cyano-2-methyl-butyric acid. The melting point of the pure recrystallized substance is 118° C.

EXAMPLE 6

A mixture of 2.5 g of 2-amino-3,3-diphenyl-5-methyl-pyrroline-(1) and 1.5 g of 3-methylpyrazole-5-carboxylic acid ethyl ester is heated for 150 minutes at 170°–180° C. (bath temperature). The homogeneous, still-warm melt is dissolved in 30 ml of methanol and the solution cooled. The reaction product is chromatographed on silica gel using a mixture of ethyl acetate and benzene (2:3) and yields a product which is identical with that obtained according to Example 2.

The following Example illustrates a typical pharmaceutical preparation containing one of the pyrazole derivatives provided by the invention:

EXAMPLE

Tablets for oral administration can contain the following ingredients:

| | |
|---|---|
| 3-Methyl-N-(5-methyl-3,3-diphenyl-1-pyrrolin-2-yl)-pyrazole-5-carboxamide | 100 mg |
| Lactose | 85 mg |
| Maize starch | 85 mg |
| Microcrystalline cellulose | 27 mg |
| Magnesium stearate | 3 mg |

We claim:
1. A process for the manufacture of a compound of the formula

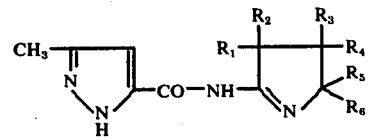

wherein $R_1$ and $R_2$ each represent phenyl, lower alkylphenyl or lower alkoxyphenyl and $R_3$, $R_4$, $R_5$ and $R_6$ each represent a hydrogen atom or a lower alkyl group which process comprises reacting a compound of the general formula

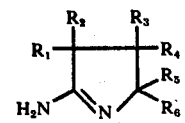

wherein $R_1$, $R_2$, $R_3$, $R_4$, $R_5$ and $R_6$ have the above significance,
with a 3-methylpyrazole-5-carboxylic acid ester or with 2,7-dimethyl-4,9-dioxo-4H,9H-dipyrazolo[1,5-a: 1',5'-d]pyrazine.

2. A process as in claim 1 wherein $R_1$ and $R_2$ are each phenyl and $R_3$, $R_4$, $R_5$ and $R_6$ are selected from the group consisting of a hydrogen atom and a methyl group is utilized as the starting material.

3. A process as in claim 1 wherein the compound of the formula II utilized is 2-amino-3,3-diphenyl-5-methyl-pyrroline-(1).

* * * * *